(12) United States Patent
Ansmann et al.

(10) Patent No.: US 6,306,916 B1
(45) Date of Patent: *Oct. 23, 2001

(54) PEARLY LUSTER CONCENTRATE WITH NEWTONIAN VISCOSITY

(75) Inventors: Achim Ansmann, Erkrath; Rolf Kawa, Monheim; Gabriele Strauss, Duesseldorf, all of (DE)

(73) Assignee: Henkel Kommanditgesellschaft auf Aktien, Duesseldorf (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/930,690

(22) PCT Filed: Mar. 20, 1996

(86) PCT No.: PCT/EP96/01198

§ 371 Date: Oct. 24, 1997

§ 102(e) Date: Oct. 24, 1997

(87) PCT Pub. No.: WO96/29981

PCT Pub. Date: Oct. 3, 1996

(30) Foreign Application Priority Data

Mar. 29, 1995 (DE) .............................................. 195 11 571

(51) Int. Cl.$^7$ ................................. A61K 7/50; B01F 3/12; C11D 1/74
(52) U.S. Cl. ............................. 516/77; 424/401; 510/138; 510/416; 514/937
(58) Field of Search ............................. 252/311; 510/416, 510/138; 424/401; 516/77; 514/937

(56) References Cited

U.S. PATENT DOCUMENTS

| 3,928,249 | | 12/1975 | Nunziata et al. | ..................... 510/237 |
|---|---|---|---|---|
| 4,668,422 | * | 5/1987 | Malik et al. | ..................... 510/416 X |
| 4,824,594 | | 4/1989 | Hoeffkes et al. | ................. 510/416 X |
| 4,948,528 | | 8/1990 | Hoeffkes et al. | ..................... 252/357 |
| 5,017,305 | | 5/1991 | Hoeffkes et al. | ..................... 252/311 |
| 5,389,282 | * | 2/1995 | Saijo et al. | ........................ 510/416 |
| 5,529,721 | | 6/1996 | Salka et al. | ..................... 510/416 X |
| 5,711,899 | * | 1/1998 | Kawa et al. | ..................... 252/311 |

FOREIGN PATENT DOCUMENTS

| 2 006 248 | 6/1990 | (CA) . |
|---|---|---|
| 2 103 578 | 8/1992 | (CA) . |
| 35 08 051 | 9/1986 | (DE) . |
| 38 43 572 | 6/1990 | (DE) . |
| 41 03 551 | 8/1992 | (DE) . |
| 195 11 574 | 11/1995 | (DE) . |
| 0 268 992 | 6/1988 | (EP) . |
| 0 300 379 | 1/1989 | (EP) . |
| 0 376 083 | 7/1990 | (EP) . |
| WO92/13512 | 8/1992 | (WO) . |
| WO94/24248 | 10/1994 | (WO) . |
| WO95/03782 | 2/1995 | (WO) . |

* cited by examiner

*Primary Examiner*—Richard D. Lovering
(74) *Attorney, Agent, or Firm*—John E. Drach; Glenn E. J. Murphy; Steven J. Trzaska

(57) ABSTRACT

The invention concerns pearly luster concentrates in the form of an aqueous dispersion having between 10 and 40 wt % pearly luster-forming components and between 15 and 55 wt % emulsifiers. The concentrates contain as emulsifiers alkylpolyglycosides of general formula (I), RO—$(Z)_x$, in which R stands for a $C_6$ to $C_{22}$ alkyl group, Z stands for a mono or oligosaccharide, x is a number from 1.1 to 5, or their addition products with 1 to 10 molecules ethylene oxide and/or propylene oxide. The concentrates are characterized by a Newtonian flow behaviour when they are free of emulsifiers with —COO$^-$ and —OSO$_3^-$ groups, such that these concentrates are considerably easier to handle.

23 Claims, No Drawings

PEARLY LUSTER CONCENTRATE WITH NEWTONIAN VISCOSITY

This application is a 371 of PCT/EP 96/01198 filed Mar. 20, 1996.

BACKGROUND OF THE INVENTION

1. Field of the Invention

This invention relates to a pearlescent concentrate with newtonian flow behavior in the form of a low-viscosity aqueous dispersion containing 10 to 40% by weight of pearlescing components.

Aqueous preparations of surfactants and cosmetic formulations can be given a pearlescent, aesthetically pleasing appearance by incorporation of substances which, after cooling, precipitate in the form of fine pearlescent crystals and remain dispersed in the preparations. Suitable pearlescing agents are, for example, the mono-, di- and optionally triesters of ethylene glycol or glycerol with $C_{14-22}$ fatty acids, oligomeric alkylene glycol esters of this type, for example PEG-3-distearates, fatty acids and monoalkanolamides of fatty acids.

It is also known that the pearlescing agents mentioned can be stably dispersed in water or in aqueous emulsifier solutions and that the concentrated pearlescing dispersions obtained in this way can be added without heating to the preparations to be given a pearlescent appearance so that there is no need for the heating and cooling otherwise necessary for incorporation to form the pearlescent crystals.

One of the problems involved in the production and use of pearlescent concentrates concerns their flowability and pumpability. Both are often seriously limited, above all where the pearlescing components and emulsifiers are present in high concentrations. Alternatively, the concentrates may even assume the form of mixtures which do not flow and also cannot be pumped by conventional equipment.

2. Discussion of Related Art

Accordingly, it was proposed in German patent applications DE 38 43 572 and DE 41 03 551 to reduce the viscosity of pearlescent concentrates by addition of low molecular weight polyhydric alcohols and thus to make them flowable and pumpable.

International patent application WO 94/24248 discloses pearlescing agents based on alkyl polyglycoside/betaine surfactants which also contain glycols.

Although pearlescent concentrates sufficiently pumpable and flowable for conventional processing can be obtained in accordance with the teachings of these documents, these products are still not entirely satisfactory. The reason for this lies in the pronounced non-Newtonian or thixotropic behavior of the concentrates.

Thus, a thixotropic increase in viscosity is observed, in particular after prolonged storage. In addition, the yield point means that a more or less thick layer of product always remains behind on the walls of the storage container and can only be removed with immense effort or in the course of cleaning operations. In the latter case, therefore, part of the product is lost, i.e. is not available for processing. Finally, the pressure loss involved in the pumping of non-newtonian liquids is distinctly higher than for newtonian liquids which means that the pumping equipment has to meet increased performance requirements, particularly at the beginning of pumping.

Accordingly, there is still a need for pearlescent concentrates which are distinguished both by low viscosities, i.e. pumpability or flowability, and in particular by newtonian viscosity behavior.

DESCRIPTION OF THE INVENTION

It has now surprisingly been found that low-viscosity pearlescent concentrates with the viscosity behavior of newtonian liquids can be formulated providing alkyl polyglycosides are used as emulsifiers. This viscosity behavior only occurs if the emulsifiers used belong predominantly to the class of alkyl polyglycosides. For example, even small quantities of emulsifiers containing —COO⁻ and —OSO₃⁻ groups generally lead to pronounced non-newtonian behavior of the pearlescent concentrates.

Accordingly, the present invention relates to a pearlescent concentrate in the form of an aqueous dispersion containing 10 to 40% by weight of pearlescing components and 15 to 55% by weight of emulsifiers, characterized in that the emulsifiers are alkyl polyglycosides corresponding to general formula (I):

$$RO—(Z)_x \quad (I)$$

in which R is an alkyl group containing 6 to 22 carbon atoms, Z is a mono- or oligosaccharide, x is a number of 1.1 to 5, or addition products thereof with 1 to 10 molecules of ethylene oxide and/or propylene oxide and in that the pearlescent concentrate is free from emulsifiers containing —COO⁻ and —OSO₃⁻ groups.

In the context of the invention, pearlescing components are understood to be fusible fats or waxes which, on cooling of their aqueous solutions or emulsions at temperatures of around 30 to 90° C., crystallize out in the form of fine pearlescent crystals.

These fusible fats or waxes include (A1) esters corresponding to formula (II):

$$R^1—(OC_nH_{2n})_x—OR^2 \quad (II)$$

in which $R^1$ is a linear fatty acyl group containing 14 to 22 carbon atoms, $R^2$ is hydrogen or has the same meaning as $R^1$, n=2 or 3 and x is a number of 1 to 4, (A2) monoalkanolamides corresponding to general formula (III):

$$R^3—CO—NH—X \quad (III)$$

in which $R^3$ is an alkyl group containing 8 to 22 and, more particularly, 8 to 18 carbon atoms and X is a group —CH₂—CH₂—OH, a group —CH₂—CH₂—CH₂—OH or a group —C(CH₃)₂—OH, (A3) linear saturated fatty acids containing 14 to 22 carbon atoms, (A4) mono-, di- and triesters of glycerol with linear saturated fatty acids containing 12 to 22 carbon atoms and (A5) β-ketosulfones corresponding to general formula (IV):

$$R^4—CO—\underset{\underset{R^5}{|}}{CH}—SO_2—CH_2—R^6 \quad (IV)$$

in which $R^4$ is an alkyl or alkenyl group containing 11 to 21 carbon atoms, $R^5$ and $R^6$ are hydrogen atoms or together represent an ethylene group which forms a tetrahydrothiophene dioxide ring with the group positioned between $R^5$ and $R^6$.

Suitable esters (A1) corresponding to the general formula $R^1(OC_nH_{2n})_xOR^2$ are, for example, the monoesters and diesters of ethylene glycol and propylene glycol with higher fatty acids, for example with palmitic acid, stearic acid or behenic acid, or the diesters of diethylene glycol or triethylene glycol with such fatty acids. Mixtures of monoesters and diesters of the glycols mentioned with fatty acid mixtures, for example with hydrogenated tallow fatty acid, palm oil fatty acid or with the saturated $C_{14-18}$ fatty acid fraction of tallow fatty acid, are also suitable. The ethylene glycol monoesters and/or diesters of palmitic and/or stearic acid are particularly suitable.

Preferred monoalkanolamides (A2) are the monoethanolamides. These compounds may contain single alkyl groups. However, it is standard practice to produce the alkanolamides from fatty acid mixtures from natural sources, for example cocofatty acids, so that corresponding mixtures of alkyl groups are present.

Suitable linear fatty acids (A3) are, for example, palmitic acid, stearic acid, arachic acid or behenic acid, although technical fatty acid cuts consisting entirely or predominantly of fatty acids containing 16 to 22 carbon atoms, for example the palmitic/stearic acid fractions obtained from tallow fatty acid or palm oil fatty acid by removal of the fatty acids liquid at +5° C. or the palmitic/stearic acid fractions obtainable by hydrogenation of tallow fatty acid or palm oil fatty acid, may also be used.

The glycerol esters (A4) suitable for use in the teaching according to the invention include the mono-, di- and—in particular—triesters with lauric acid, myristic acid, palmitic acid, stearic acid and behenic acid and with mixtures of these fatty acids.

The β-ketosulfones (A5) corresponding to general formula (IV) have the advantage over known ethylene glycol monoesters and diesters that the pearlescence of the formulations has higher thermal stability, i.e. the formulations retain their pearlescence for several hours on heating to temperatures above 50° C. and, in some cases, even to temperatures above 70° C. Further information on the β-ketosulfones mentioned can be found in German patent application DE 35 08 051.

The pearlescent concentrates according to the invention may contain both exclusively representatives of one of these classes of compounds and mixtures of representatives of several of these classes of compounds.

Preferred pearlescing components are representatives of classes (A1) to (A4).

However, fatty acid monoalkanolamides or dialkanolamides, i.e. pearlescing components of group (A2), and derivatives thereof have recently been suspected of involvement in the formation of nitrosamines. Accordingly, it may be desirable to formulate cosmetic preparations without such alkanolamines and alkanolamine derivatives. For this reason, compounds belonging to classes (A1), (A3) and (A4) may be particularly preferred pearlescing components.

Pearlescent concentrates in which at least 50% by weight and, more particularly, at least 70% by weight of the pearlescing components consist of ethylene glycol distearate are most particularly preferred.

The pearlescent concentrates according to the invention contain alkyl polyglycosides as sole or principal emulsifiers.

The alkyl polyglycosides corresponding to formula (I) are characterized by the following parameters:

The alkyl group R contains 6 to 22 carbon atoms and may be both linear and branched. Primary linear and 2-methyl-branched aliphatic groups are preferred. Corresponding alkyl groups are, for example, 1-octyl, 1-decyl, 1-lauryl, 1-myristyl, 1-cetyl and 1-stearyl. 1-Octyl, 1-decyl, 1-lauryl, 1-myristyl are particularly preferred. Where so-called "oxoalcohols" are used as starting materials, compounds containing an odd number of carbon atoms in the alkyl chain predominate.

The alkyl polyglycosides suitable for use in accordance with the invention may contain only one particular alkyl group R. However, these compounds are normally prepared from natural fats and oils or mineral oils. In this case, the alkyl groups are mixtures corresponding to the starting compounds or corresponding to the particular working-up of these compounds.

Particularly preferred alkyl polyglycosides are those in which R consists essentially of $C_8$ and $C_{10}$ alkyl groups,
essentially of $C_{12}$ and $C_{14}$ alkyl groups,
essentially of $C_8$ to $C_{16}$ alkyl groups, or
essentially of $C_{12}$ to $C_{16}$ alkyl groups.

Any mono- or oligosaccharides may be used as the sugar unit Z. Sugars containing 5 or 6 carbon atoms and the corresponding oligosaccharides are normally used. Corresponding sugars are, for example, glucose, fructose, galactose, arabinose, ribose, xylose, lyxose, allose, altrose, mannose, gulose, idose, talose and sucrose. Preferred sugar units are glucose, fructose, galactose, arabinose and sucrose. Glucose is particularly preferred.

The alkyl polyglycosides suitable for use in accordance with the invention contain on average 1.1 to 5 sugar units. Alkyl glycosides in which x is a number of 1.1 to 2 are preferred. Alkyl glycosides in which x is a number of 1.1 to 1.4 are particularly preferred.

The alkoxylated homologs of the alkyl polyglycosides mentioned may also be used in accordance with the invention. These homologs may contain on average up to 10 ethylene oxide and/or propylene oxide units per alkyl glycoside unit. These products are also not normally individual compounds, but instead have a homolog distribution corresponding to the ethoxylation processes selected. These alkoxylated compounds may be obtained, for example, by using ethoxylated fatty acids in the synthesis of the alkyl polyglycosides. However, it is preferred to use the non-alkoxylated compounds for the teaching according to the invention.

As already mentioned, the newtonian viscosity behavior of the pearlescent concentrates is attributable to the use of alkyl polyglycosides as emulsifiers. However, it has also been found that, in a number of cases, the addition of other emulsifiers does not result in the loss of this viscosity behavior. The emulsifiers in question are, in particular, other nonionic emulsifiers. In many cases, they may be present in quantities of up to 50% by weight and, more particularly, in quantities of up to 20% by weight, based on the quantities of alkyl polyglycoside, without inducing non-newtonian viscosity behavior.

Suitable nonionic emulsifiers contain, for example, a polyol group, a polyalkylene glycol ether group or a combined polyol/polyglycol ether group as the hydrophilic group. Examples of such compounds are adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group, $C_{12-22}$ fatty acid monoesters and diesters of adducts of 1 to 30 moles of ethylene oxide with glycerol, sorbitan monoesters and diesters of saturated and unsaturated $C_{8-22}$ fatty acids and ethylene oxide adducts thereof and addition products of 5 to 60 moles of ethylene oxide with castor oil and hydrogenated castor oil.

Mixtures of compounds from several of these classes are also suitable.

In addition, cationic emulsifiers have also proved to be suitable other emulsifiers in a number of cases.

Finally, anionic emulsifiers containing a phosphate group as the ionic group may also generally be used for the purposes of the invention.

In cases where it is intended to use other emulsifiers in addition to the alkyl polyglycosides, the expert will be able—within the scope of the present teaching—routinely to test the particular systems for newtonian viscosity behavior using any of the processes known to him for measuring viscosity.

The compounds containing alkyl groups used as emulsifiers may be individual substances. In general, however, these substances are produced from native vegetable and animal raw materials so that mixtures with different alkyl chain lengths according to the particular raw material are obtained.

Among the emulsifiers representing addition products of ethylene and/or propylene oxide with fatty alcohols, it is possible to use both products with a "normal" homolog distribution and those with a narrow homolog distribution. By "normal" homolog distribution are meant mixtures of homologs which are obtained in the reaction of fatty alcohol and alkylene oxide using alkali metals, alkali metal hydroxides or alkali metal alcoholates as catalysts. By contrast, narrow homolog distributions are obtained where hydrotalcites, alkaline earth metal salts of ether carboxylic acids, alkaline earth metal oxides, hydroxides or alcoholates, for example, are used as catalysts. It may be preferable to use so-called "narrow-range" products, i.e. products with a narrow homolog distribution.

According to the invention, pearlescing concentrates containing 20 to 30% by weight of pearlescing components and 15 to 45% by weight of emulsifiers have proved to be particularly advantageous.

In addition, the pearlescent concentrates according to the invention may optionally contain a low molecular weight polyhydric alcohol.

Low molecular weight polyhydric alcohols belonging to a preferred group contain 2 to 12 carbon atoms and 2 to 10 hydroxyl groups. Corresponding alcohols are, for example, ethylene glycol, 1,2- and 1,3-propylene glycol, glycerol, erythritol, arabitol, adonitol, xylitol, sorbitol, mannitol, dulcitol, glucose and sucrose. The use of glycerol, 1,2-propylene glycol, 1,3-propylene glycol, sorbitol and/or glucose is particularly preferred.

The use of glycerol as a low molecular polyhydric alcohol leads to pearlescent concentrates which give the end products a particularly brilliant pearlescence.

Another group of preferred low molecular weight polyhydric alcohols is formed by oligomeric ethers based in particular on ethylene glycol, propylene glycol and glycerol. Products with an average molecular weight below about 700 dalton are particularly suitable. The di-, tri- and tetramers of ethylene glycol and glycerol above all may be used in accordance with the invention.

According to the invention, the low molecular weight polyhydric alcohols are preferably used in quantities of 0.1 to 15% by weight, based on the preparation as a whole.

Apart from the above components, the pearlescent concentrates according to the invention essentially contain water.

In addition, they may contain small quantities of buffers to adjust the pH to a value of 2 to 8, for example citric acid and/or sodium citrate, and inorganic salts, for example sodium chloride, as thickeners.

In a first preferred embodiment, the pearlescent concentrates according to the invention contain the usual preservatives well-known to the expert. Corresponding preservatives are, for example, formic acid, benzoic acid and pHB esters.

In a second preferred embodiment, the pearlescent concentrates are preservative-free. Preservative-free in this context means that no preservatives are added to the concentrates. Accordingly, they preferably contain no preservatives or only those quantities of preservatives which are introduced with the individual raw materials selected.

The pearlescent concentrates according to the invention are readily pumpable and storable for long periods, i.e. at least about 6 months, at temperatures of at least 15 to 30° C.

The pearlescent concentrates according to the invention may be prepared by first heating components (A), (B) and (C) together to a temperature about 1 to 30° C. above the melting point. In most cases, this will be a temperature of around 60 to 90° C. The water heated to substantially the same temperature is then added to this mixture. If an ionic water-soluble emulsifier is used as the emulsifier, it may be preferable to dissolve it in the water phase and to introduce it into the mixture together with the water. The aqueous phase may already contain the buffers in dissolved form. The dispersion formed is then cooled with continuous stirring to room temperature, i.e. to around 25° C. In the majority of cases, the viscosity of the pearlescent concentrate is so low that there is no need to use special stirring units, such as homogenizers or other high-speed mixers.

The pearlescent concentrates according to the invention are suitable for the production of opaque and pearlescent, liquid aqueous preparations of water-soluble surfactants. For example, they may be incorporated in liquid detergents and cleaning products, such as dishwashing detergents, liquid light-duty detergents and liquid soaps, although they are preferably incorporated in liquid personal hygiene and body-care formulations, for example shampoos, liquid hand and body soaps, shower bath formulations, bath additives (foam baths), hair rinses or hair colorants.

To produce pearlescence, the pearlescent concentrates according to the invention are added to the clear aqueous preparations at 0 to 40° C. in a quantity of 1 to 10% by weight and, more particularly, in a quantity of 1.5 to 5% by weight, based on the preparation, and dispersed therein by stirring. An extremely dense pearlescence with a metallic sheen and a brilliant to light sparkle is obtained according to the preparation and the concentration used.

The following Examples are intended to illustrate the invention without limiting it in any way.

EXAMPLES

1. Pearlescent concentrates

Pearlescent concentrates with the compositions shown in Table 1 were prepared.

TABLE 1

Flowable Pearlescent Concentrates

| Components | Mixture No. Content [% by weight] | | | | | |
|---|---|---|---|---|---|---|
| | 1 | 2 | 3 | 4 | 5 | 6 |
| Pearlescer: | | | | | | |
| Cutina ® AGS[1] | 20 | 20 | 20 | — | 20 | 15 |
| Cutina ® GMS[2] | — | — | — | 15 | — | — |
| Comperlan ® 100[3] | — | — | 3 | 5 | — | 5 |
| Cutina ® FS 45[4] | — | — | — | 2 | — | — |
| Emulsifier: | | | | | | |
| Plantaren ® H 1200[5] | 40 | 30 | 40 | 30 | 45 | 30 |
| Dehydol ® KS4[6] | — | 5 | — | — | — | — |
| Texapon ® N70[7] | — | — | — | 5 | — | — |
| Cetiol ® HE[8] | — | — | — | 1 | — | — |
| Alcohol: | | | | | | |
| Glycerol[9] | — | 10 | — | — | 15 | — |
| 1,2-Propylene glycol | 7 | — | — | — | — | — |
| Sorbitol | — | — | — | 10 | — | — |
| Glucose | — | — | — | — | — | 13 |
| Water, viscosity and pH regulators | ←to 100 → | | | | | |

[1]Ethylene glycol distearate (at least 90% diester; CTFA name: Glycol Distearate) (HENKEL)
[2]Glycerol monostearate (monoester content about 50%; CTFA name: Glyceryl Stearate) (HENKEL)
[3]Cocofatty acid monoethanolamide (about 95% amide; CTFA name: Cocamide MEA) (HENKEL) Composition of the fatty acid: ca. 56% lauric acid ca. 21% myristic acid ca. 10% palmitic acid ca. 13% stearic acid and oleic acid
[4]$C_{16-18}$ fatty acid (CTFA name: Palmitic Acid (and) Stearic Acid) (HENKEL)
[5]$C_{12-16}$ fatty alcohol-1,4-glucoside (about 50% active substance in water; CTFA name: Lauryl Polyglycose) (HENKEL CORP.)
[6]$C_{12-14}$ fatty alcohol + 4 ethylene oxide (HENKEL)
[7]Sodium lauryl ether sulfate (about 72% active substance in water; CTFA name: Sodium Laureth Sulfate) (HENKEL)
[8]Polyol fatty acid ester (CTFA name: PEG-7-Glyceryl Cocoate) (HENKEL)
[9]86% in water

What is claimed is:

1. A pearlescent concentrate having newtonian viscosity, consisting essentially of an aqueous dispersion of 10% to 40% by weight of a pearlescing component and 15% to 55% by weight of an alkyl polyglycoside of the formula (I):

$$RO-(Z)_x \qquad (I)$$

wherein R is $C_6$ to $C_{22}$ alkyl, Z is a mono- or oligosaccharide, and x is a number of 1.1 to 5, and wherein the concentrate is free from emulsifiers containing —COO⁻ and —OSO₃⁻ groups.

2. A pearlescent concentrate according to claim 1, wherein the alkyl polyglycoside is alkoxylated with 1 to 10 ethylene oxide or propylene oxide units per alkyl glycoside unit.

3. A pearlescent concentrate according to claim 1, wherein R is 1-octyl, 1-decyl, 1-lauryl, 1-myristyl, 1-cetyl, or 1-stearyl.

4. A pearlescent concentrate according to claim 1, wherein Z is selected from the group consisting of glucose, fructose, galactose, arabinose, ribose, xylose, lyxose, allose, altrose, mannose, gulose, idose, talose, and sucrose.

5. A pearlescent concentrate according to claim 4, wherein Z is selected from the group consisting of glucose, fructose, galactose, arabinose, and sucrose.

6. A pearlescent concentrate according to claim 1, wherein x is a number of 1.1 to 2.

7. A pearlescent concentrate according to claim 6, wherein x is a number of 1.1 to 1.4.

8. A pearlescent concentrate according to claim 1 consisting essentially of up to 50% by weight based on the weight of alkyl polyglycoside of a nonionic emulsifier other than said alkyl polyglycoside.

9. A pearlescent concentrate according to claim 8 consisting essentially of up to 20% by weight based on the weight of alkyl polyglycoside of a nonionic emulsifier other than said alkyl polyglycoside.

10. A pearlescent concentrate according to claim 1, wherein the pearlescing component comprises a compound selected from the group consisting of:
   (a) esters of the formula (II)

$$R^1-(OC_nH_{2n})_x-OR^2$$

wherein $R^1$ is $C_{14}$ to $C_{22}$ linear fatty acyl, $R^{12}$ is $R^1$ or hydrogen, n is 2 or 3, and x is a number of 1 to 4;
   (b) monoalkanolamides of the formula (III)

$$R^3-CO-NH-X$$

wherein $R^3$ is $C_8$ to $C_{22}$ alkyl and X is —CH₂—CH₂—OH, —CH₂—CH₂—CH₂—OH, or —C(CH₃)₂—OH;
   (c) $Cl_{14}$ to $C_{22}$ linear saturated fatty acids;
   (d) mono-, di-, and triesters of glycol with $C_{12}$ to C22 linear saturated fatty acids; and
   (e) β-ketosulfones of the formula (IV)

$$R^4-CO-\underset{\underset{R^5}{|}}{CH}-SO_2-CH_2-R^6 \qquad (IV)$$

wherein $R^4$ is $C_{11}$ to $C_2$, alkyl or alkenyl and $R^5$ and $R^6$ are hydrogen or together form a tetrahydrothiophene dioxide ring.

11. A pearlescent concentrate according to claim 10 consisting essentially of 20% to 30% by weight of the pearlescing component and 15% to 45% by weight of alkyl polyglycoside.

12. A pearlescent concentrate according to claim 11 consisting essentially of 15% to 40% by weight of alkyl polyglycoside.

13. A pearlescent concentrate according to claim 10 consisting essentially of at least 50% by weight based on the weight of pearlescing component of ethylene glycol distearate.

14. A pearlescent concentrate according to claim 13 consisting essentially of at least 70% by weight based on the weight of pearlescing component of ethylene glycol distearate.

15. A pearlescent concentrate according to claim 10 consisting essentially of a low molecular weight polyhydric alcohol.

16. A pearlescent concentrate according to claim 15 consisting essentially of 0.1% to 15% by weight of the low molecular weight polyhydric alcohol.

17. A pearlescent concentrate according to claim 16, wherein the polyhydric alcohol has 2 to 12 carbon atoms and 2 to 10 hydroxyl groups.

18. A pearlescent concentrate according to claim 16, wherein the polyhydric alcohol is selected from the group consisting of glycerol, 1,2-propylene glycol, 1,3-propylene glycol, glucose, and sorbitol.

19. A pearlescent concentrate according to claim 16, wherein the polyhydric alcohol is selected from the group consisting of polyethylene glycols, polypropylene glycols, and polyglycerols having an average molecular weight below 700 dalton.

20. A pearlescent liquid aqueous surfactant preparation comprising 0.5% to 10% by weight of the pearlescing concentrate of claim 10.

21. A pearlescent liquid aqueous surfactant preparation comprising 1.5% to 5% by weight of the pearlescing concentrate of claim 10.

22. A process for preparing a clouded or pearlescent aqueous preparation of water-soluble surfactants comprising the steps of adding to the preparation 0.5% to 10% by weight of the pearlescing concentrate of claim 10 at a temperature of 0° C. to 40° C. and stirring to disperse the concentrate in the preparation.

23. A process according to claim 22, wherein 1.5% to 5% by weight of the pearlescing concentrate is added to the preparation.

* * * * *